United States Patent [19]

Nathanson

[11] Patent Number: 4,652,586
[45] Date of Patent: Mar. 24, 1987

[54] SELECTIVE BETA-2 ADRENERGIC ANTAGONISTS FOR THE TREATMENT OF GLAUCOMA

[75] Inventor: James A. Nathanson, Boston, Mass.

[73] Assignee: The General Hospital Corporation, Boston, Mass.

[21] Appl. No.: 204,819

[22] Filed: Nov. 7, 1980

[51] Int. Cl.$^4$ .............................................. A61K 31/15
[52] U.S. Cl. .................................... 514/640; 514/913
[58] Field of Search ................. 424/327; 514/640, 913

[56] References Cited

U.S. PATENT DOCUMENTS 3,989,844 11/1976 Schutz et al. ........................ 424/237

FOREIGN PATENT DOCUMENTS 0003644 8/1979 European Pat. Off. .

OTHER PUBLICATIONS

Brit. J. Ophthal., 59 296–300 (1975)—Elliot et al.
Brit. J. Ophthal., 59, 301–303 (1975)—Bonomi et al.
Invest. Ophthal., 15(6) (1976), pp. 489–492—Katz et al.
Zimmerman et al., Survey of Ophthalmology, 23: 347–362 (1977).

Primary Examiner—Douglas W. Robinson
Attorney, Agent, or Firm—Saidman, Sterne, Kessler & Goldstein

[57] ABSTRACT

A method of decreasing the intraocular pressure in the eye of an animal which comprises administering to the animal an intraocular pressure decreasing amount of a beta$_2$ adrenergic receptor antagonist having a $\beta_2/\beta_1$ potency ratio of at least 10. The method is particularly useful for the treatment of glaucoma in humans.

3 Claims, 3 Drawing Figures

SELECTIVE BETA-2 ADRENERGIC ANTAGONISTS FOR THE TREATMENT OF GLAUCOMA

BACKGROUND OF THE INVENTION

1. Field of the Invention

The present invention relates to the use of selective beta-2 adrenergic antagonists for the decrease of intraocular pressure in animals, especially humans, particularly for the treatment of glaucoma.

2. Description of the Prior Art

Open angle glaucoma is a progressive disorder of increased intraocular pressure (IOP) which results from excess accumulation of aqueous humor, a fluid which is formed by the ciliary processes in the posterior ocular chamber, and which normally leaves the eye through the trabecular meshwork and Schlemm's canal, located in the lateral angle of the anterior chamber.

Considerable evidence suggests that the adrenergic nervous system plays a significant but complex role in the regulation of intraocular pressure. Sympathetic nerve fibers innervate the ciliary process and trabecular meshwork, and both sympathetic stimulation and locally applied beta-adrenergic agonists, such as epinephrine, reduce intraocular pressure. Beta-adrenergic antagonists, such as timolol (which is effective clinically in treating glaucoma) also reduce intraocular pressure. (Zimmerman, T. J. and Boger, W. P. III, Surv. Opthal. 23: 347-362 (May-June, 1979)).

Adrenergic receptors are generally divided into three groups: alpha adrenergic receptors (mediating smooth muscle contraction), beta$_1$ adrenergic receptors (mediating cardiac acceleration and fatty acid mobilization), and beta$_2$ adrenergic receptors (mediating smooth muscle relaxation). Biochemical studies prior to this invention have not indicated whether there are beta-adrenergic receptors in the ciliary processes or trabecular meshwork separate from those in the neighboring iris, which also receives adrenergic innervation. Furthermore, in the ciliary processes themselves, it is not certain whether there are betareceptors in the secretory epithelium distinct from those on ciliary blood vessels. It also remained to be seen prior to this invention whether any beta receptors present would be beta$_1$ or beta$_2$. Such studies, which are disclosed in the present patent application, serve to more clearly ascertain the type of agent ideally useful for the treatment of glaucoma.

As mentioned previously, Zimmerman and Boger, supra, have described the use of timolol, a beta adrenergic antagonist, for the reduction of intraocular pressure, as part of a review on the general use of beta-adrenergic blocking agents in the treatment of glaucoma. These authors describe the use of such beta blockers as dichloroisoproterenol (DCI), pronethalol and propranolol. The latter, introduced in 1964, was until recently the only beta blocking agent released for clinical use in the United States, although more than eighteen drugs of this class are in current use overseas. In 1968, practolol was developed as the first beta blocking agent which selectively inhibits cardiac receptors (beta$_1$). Atenolol, another selective beta$_1$ blocker, was synthesized in 1973; in the intervening years, other similar molecules with beta$_1$ selectivity have come to light. Timolol, recently released for topical opthalmic use, is the first beta$_2$ blocker released for such use in this country. Several side effects have been found for these prior art beta blockers. Topical application of propranolol causes ocular discomfort and stinging thus limiting its use in eyedrops. Practolol, while decreasing intraocular pressure, has received somewhat less attention after recognition that it causes ocular mucocutaneous syndrome. Timolol, a non-selective beta antagonist, is a promising medication for the treatment of glaucoma and appears to be more effective in lowering IOP than any of the other topical agents while being better tolerated (Zimmerman and Boger, supra, at page 358). Yet to be defined, however, is a possible significant loss of efficacy in some patients using this medication for extended periods. The authors recommend using timolol with caution in patients with cardiovacular diseases, such as bradycardia, second degree heart block or heart failure, and in patients with asthma.

Colasanti and Trotter (Journal of Investigative Opthalmology and Visual Science, 18:24 (1979)), disclose the use of H35/25, described as a "selective $\beta_2$-antagonist" for the decrease of intraocular tension in adult female cats. They demonstrate that H35/25 had about the same maximal reduction as timolol, described as a "mixed $\beta_1$- and $\beta_2$-antagonist", and somewhat lesser effect than salbutamol, described as a "selective $\beta_2$ antagonist". The classification of adrenoceptor agents as $\beta_1$ or $\beta_2$ has, however, recently been further clarified through the extensive work of Minneman and co-workers (Minneman, K. E. et al, Molecular Pharmacology 16:33 (1979); and Journal of Pharmacology and Experimental Therapeutics Vol. 211:502-508 (1979)). These workers demonstrated that, contrary to the definition of H35/25 as a "selective $\beta_2$ antagonist", this drug shows no specificity for $\beta_1$ or $\beta_2$ adrenergic receptors. This observation is consistent with Colasanti's observation that H35/25 and timolol show about the same effects on intraocular pressure, timolol also being a non-specific adrenoceptor antagonist.

In view of the many side effects brought about by the agents currently used for the decrease of intraocular pressure in glaucoma, a need continues to exist for a highly specific family of intraocular pressure-decreasing agents.

SUMMARY OF THE INVENTION

It is therefore an object of the invention to provide highly specific and selective agents for the decrease of intraocular pressure in animals, particularly humans, especially for the treatment of glaucoma in humans.

Another object of the invention is to provide a method for the decrease of intraocular pressure in animal eyes, especially in human eyes.

Yet another object of the invention is to provide compositions useful for causing the decrease of intraocular pressure in animal, especially human, eyes.

These and other objects of the invention, as will hereinafter become more readily apparent, have been attained by providing:

A method for the decrease of intraocular pressure in the eye of an animal, especially a human, which comprises applying to said eye an intraocular pressure decreasing amount of a $\beta_2$ adrenergic receptor antagonist having a $\beta_2/\beta_1$ potency ratio of at least 10.

Other objects of the invention have been attained by providing a composition comprising an intraocular pressure decreasing amount of a $\beta_2$ adrenoceptor antagonist having a $\beta_2/\beta_1$ potency ratio of at least 10, together with a pharmacologically inert carrier.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
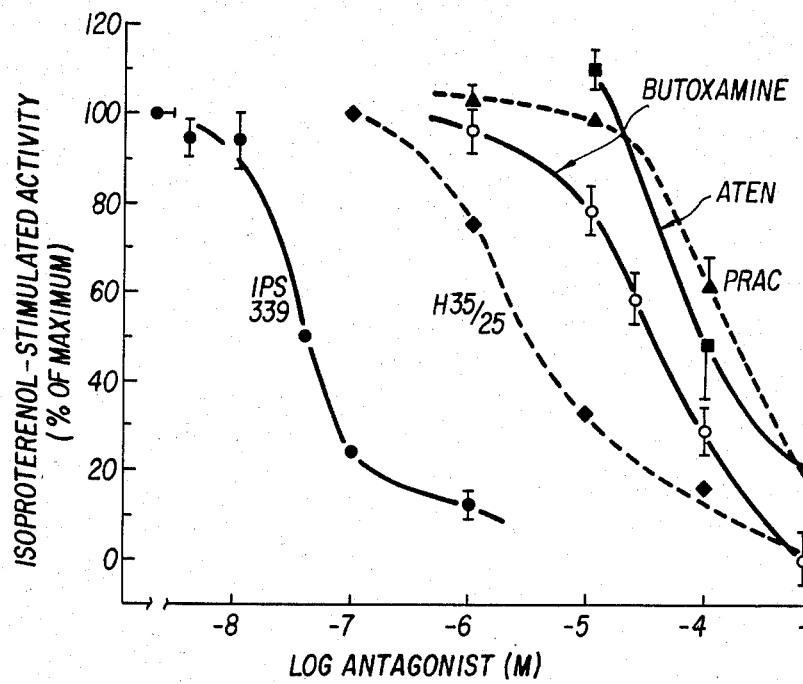
FIG. 1 shows the effects of selective $\beta_1$ and $\beta_2$ adrenergic antagonists on rabbit ciliary process adenylate cyclase activity. Stimulation, above that seen in the presence of antagonist alone, is expressed as a percentage of the stimulation seen in the presence of $3 \times 10^{-6}$M isoproterenol alone. Abbreviations are: IPS 339:(t-butyl-amino 3-ol-2-propyl)oximino-9 fluorene, hydrochloride; H35/25: (1(4'-methyl phenyl)-2-isopropyl amino propanol)); aten: atenolol; prac: practolol.

The present invention arises directly out of the discovery by the present inventor that the ocular mammalian ciliary process, including the human eye ciliary process, contains specific $\beta_2$-adrenergic receptors. Because of this discovery, it is now possible for the first time to design clinically effective $\beta_2$ adrenergic antagonists useful for decreasing intraocular pressure in mammalian eyes. The finding of the exclusive existence or predominant existence of $\beta_2$-adrenoceptors in mammalian ciliary process, indicates that $\beta_2$-adrenergic antagonists having high specificity for $\beta_2$ adrenoceptors can be effective for the treatment of glaucoma, with fewer potential side effects on tissues containing $\beta_1$ receptors, such as heart. Timolol, a nonspecific $\beta_1/\beta_2$ antagonist, has shown such troublesome side effects on heart tissue. The present invention therefore provides, for the first time, a class of agents for the treatment of glaucoma which are more potent than the agents of the prior art and, even if of similar potency, are agents with greater selectivity and substantially decreased side effects.

The discovery that the ciliary process of the mammalian eye contains $\beta_2$-adrenergic receptors is based on the technique of measuring adenylate cyclase, an enzyme which synthesizes cyclic AMP from ATP. It has been established that receptor binding of beta adrenergic agonists is associated with a concomitant activation of adenylate cyclase. (Robison, G. A., et al, Cyclic AMP, Academic Press, New York, 1971, and Wolfe, B. B., et al, Annual Reviews of Pharmacology and Toxicology, 17:575-604 (1977)). Data from a number of tissues indicates that the characteristics of binding of beta-adrenergic agonists and antagonists to the beta-adrenergic receptor are quite similar to the ability of these compounds to either activate adenylate cyclase or to block the stimulation of the enzyme by beta-agonists (Minneman, K. P., et al, Journal of Pharmacology and Experimental Therapeutics, 211:502-508 (1979)). Beta adrenergic sensitive adenylate cyclase activity was thus identified and characterized in the ocular tissues of several mammalian species such as rabbits, cats, dogs, monkeys and humans. After isolation of the ciliary process, adenylate cyclase activity was measured, and its activation by agonists or inhibition by antagonists was measured. Inhibitor constants ($K_i$) for various adrenergic blockers were calculated from the equation, $K_i = (IC_{50})/(1+S/K_a)$ (equation 1) where $IC_{50}$ was the concentration of antagonists necessary to give 50% inhibition of isoproterenol (a beta-adrenergic agonist)—stimulated activity, S was the concentration of isoproterenol present, and $K_a$ was the concentration of isoproterenol ($3.6 \times 10^{-7}$M) necessary for half maximal activation of rabbit ciliary process adenylate cyclase activity (Chen, Y. - C. and Prussoff, W. H., Biochemical Pharmacology, 22:3099-3188 (1973)).

Isoproterenol was first shown to cause substantial stimulation of ciliary process enzyme activity and much less stimulation on ciliary body and iris. Maximal stimulation for ciliary process was 331±44% of basal activity in the rabbit, and 1020% in the human. For ciliary body, maximal stimulation was 15% of the stimulation seen in the ciliary process, and for iris, maximal stimulation was 22% for that seen in the ciliary process. Epinephrine, a mixed but predominantly beta-adrenergic agonist, was about tenfold less potent than isoproterenol for human ciliary process; norepinephrine, a mixed $\alpha$-$\beta$ adrenergic agonist was about 7-fold less potent than epinephrine. At high concentrations, maximal stimulations by both norepinephrine and epinephrine were similar to that caused by isoproterenol. The same order of potency (i.e., isoproterenol > epinephrine > norepinephrine > phenephrine (an $\alpha$-adrenergic agonist)) has been observed for rabbits. This data indicates the stimulation, in the ciliary process, of a $\beta_2$-adrenergic receptor similar to that predominating in vascular and bronchial smooth muscle. The order of potency is not consistent with that found for beta adrenergic receptors present in heart, fat, and small intestine ($\beta_1$ receptors).

Figure 3:
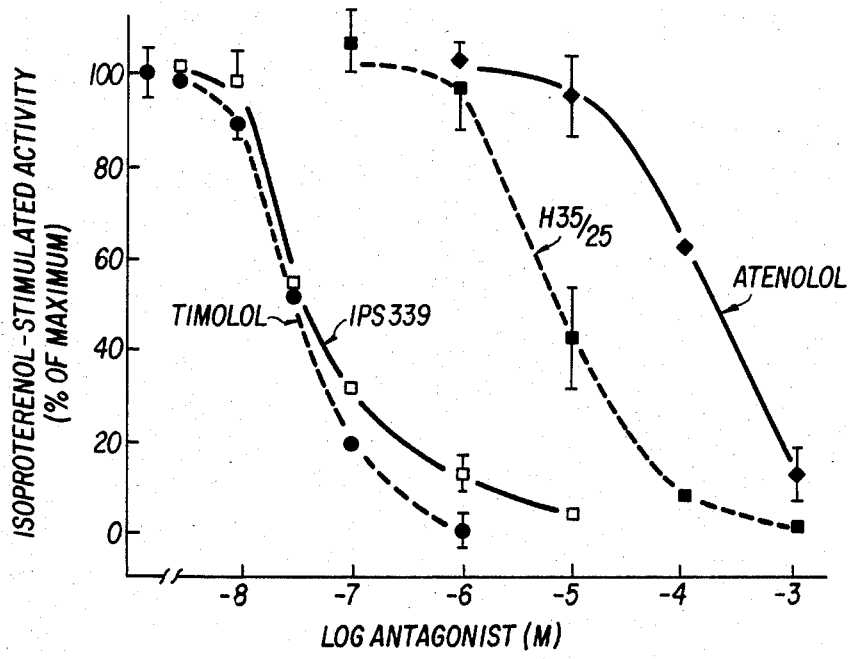
FIG. 3 shows the effect of adrenergic antagonists on human ciliary process adenylate cyclase activity. Shown is the degree of enzyme activity observed in the presence of $3 \times 10^{-6}$M isoproterenol with increasing concentrations of antagonists. Stimulation, above that seen in the presence of antagonist alone, is expressed as a percentage of that seen with isoproterenol alone (38.4±1.0 pmol/mg protein/min).

The stimulation of human ciliary process adenylate cyclase by isoproterenol is inhibited by low concentrations of the nonspecific beta adrenergic antagonist, timolol (FIG. 3). The calculated inhibitory constant ($K_i$) for timolol was $3.1 \times 10^{-9}$M. IPS 339, a compound which is found to have considerable specificity in blocking the beta$_2$ adrenergic receptor (Imbs, et al, British Journal of Pharmacology, 60:357-362 (1977)) is also a very potent inhibitor of isoproterenol stimulation, with a calculated $K_i$ of $3.4 \times 10^{-9}$M. H35/25, a beta-adrenergic blocker with some $\beta_2$ selectivity, is also effective in inhibiting ciliary beta-adrenergic-sensitive adenylate cyclase activity, with a $K_i$ of $7.4 \times 10^{-7}$M. On the other hand, atenolol, which is known to be a potent beta$_1$ adrenergic blocker in other tissues, is much less potent in the human ciliary process, with a calculated $K_i$ of $1.5 \times 10^{-5}$M.

TABLE 1 shows the pharmacological characteristics of rabbit and human ciliary process beta-adrenergic receptors compared with corresponding data from various other tissues.

TABLE I

Pharmacological characteristics of human ciliary process beta-adrenergic receptors compared with corresponding data from various other tissues and species.

| | Adenylate Cyclase $K_a$ or $K_i$ (μM) | | | $K_d$ for IHYP* Binding (μM) | | Adenylate Cyclase $K_a$ or $K_i$ (μM) | |
|---|---|---|---|---|---|---|---|
| | Ciliary Process | | Choroid | | | | |
| Agent | Human (A) | Rabbit (B) | Plexus (C) | Lung§ (D) | Heart§ (E) | Lung§ (F) | Heart§ (G) |
| Agonists | | | | | | | |
| Norepinephrine | 22.0 | 29.0 | 25.0 | 9.18 | 0.82 | 7.75 | 1.1 |
| Epinephrine | 3.0 | 2.4 | 1.55 | 1.46 | 0.90 | 0.60 | 1.5 |
| Isoproterenol | 0.33 | 0.36 | 0.14 | 0.10 | 0.05 | 0.18 | 0.12 |
| Zinterol | — | 0.04 | — | 0.02 | 1.03 | 0.065 | NE+ |
| Antagonists | | | | | | | |
| Practolol | — | 21.0 | — | 26.0 | 1.10 | 9.5 | 6.8 |
| Atenolol | 14.9 | 11.0 | 5.8 | 6.8 | 1.59 | 1.75 | 4.1 |
| Butoxamine | — | 1.40 | — | 3.55 | 7.03 | 1.35 | 9.5 |
| H35/25 | 0.74 | 0.79 | 0.14 | 0.84 | 1.97 | 0.85 | 7.0 |
| IPS 339 | 0.0034 | 0.004 | 0.0019 | 0.0005 | 0.01 | — | 0.84++ |
| Timolol | 0.0031 | 0.0045 | — | — | — | — | 0.016 |
| Propanolol | — | 0.0049 | — | 0.0006 | 0.0017 | 0.0014 | 0.025 |

*IHYP: $^{125}$I—iodohydroxybenzylpindolol;
§Heart and lung data from Minneman et al J. Pharmacol. Exp. Ther. 211: 502–508 (1979); Mol. Pharmacol. 16: 21–33 (1979) Comparisons, between columns, of drug potencies yielded the following Pearson correlation coefficients: A vs B (r = −.92, p < .01; A vs C (r = .96; p < .01); A vs D (r > .99; p < .01); A vs E (R = −.16; not significant); +no effect as agonist.
++present invention This table compares the $K_a$'s and $K_i$'s of the agonists and antagonists in affecting human and rabbit ciliary process beta-adrenergic sensitive adenylate cyclase (columns A and B). Comparison between rabbit and human ciliary process shows a significant positive correlation (r=0.92, p<0.01). The human ciliary process also shows receptor characteristics quite similar to those for the beta$_2$ adrenergic receptor present in mammalian lung (column D; r>0.99, p<0.01) but different from those of the beta$_1$-adrenergic receptor present in mammalian heart (Column E; r=−0.16, no significant correlation). The data in Column C (r=0.96; p<0.01) indicate that the beta-adrenergic sensitive adenylate cyclase present in mammalian choroid plexus also shows receptor characteristics very much like those found in the ciliary process. This latter similarity is of interest since the choroid plexus, like the ciliary process, is involved in fluid secretion which may be under adrenergic control. The Table shows additional prior art data (Minneman et al, supra) for beta adrenergic activation and inhibition of lung and heart adenylate cyclase activity (Columns F and G). As with binding data, there is much better correlation between the ciliary and lung enzymes, than between the ciliary and heart enzymes. In summary, the data provides the first direct biochemical demonstration that the human, rabbit and other mammalian ciliary processes contain beta$_2$-adrenergic receptors. Binding of adrenergic agonists to the receptors results in the activation of adenylate cyclase and the synthesis of cyclic AMP. Comparison of the relative potencies of the various agonists and antagonists tested indicates that the majority of the ciliary process beta-adrenergic receptors have characteristics like those of beta$_2$-adrenergic receptors present in mammalian lung. Because many tissues contain a mixture of receptor subtypes, however, it is not possible to rule out entirely a small percentage of beta$_1$ receptors.

This discovery by the present inventor is of great clinical interest since it indicates that potent beta$_2$ adrenergic antagonists are effective as specific beta blockers in decreasing intraocular pressure. The beta$_2$ antagonists used in the present invention are those having a $\beta_2/\beta_1$ potency ratio of at least 10. The $\beta_2/\beta_1$ potency ratio is the ratio of $K_i$ values (inhibitory constants) or $K_d$ values (disassociation constants) of antagonists for beta$_1$ versus beta$_2$ receptors. A ratio of 10 indictes that a compound is 10 times more potent as a beta$_2$ antagonist than as a beta$_1$ antagonist. The $K_i$ or $K_d$ values of beta$_1$ and beta$_2$ selective drugs for beta$_1$ and beta$_2$ adrenergic receptors are determined by evaluating tissues containing a majority of beta$_1$ receptors (e.g., cat and guinea pig heart), and tissues containing a majority of beta$_2$ receptors (e.g., rabbit ciliary process, rat liver, cat choroid plexus or lung). The determination of $K_i$ values (through measurement of adenylate cyclase) and $K_d$ values (through radioligand binding) for these different types of tissues is extensively disclosed in Nathanson, Science 204:843–844 (1979); Nathanson, Life Sciences 26:1793–1799 (1980); Minneman et al, Molecular Pharmacology 16:21–23 (1979); and Minneman et al, Journal of Pharmacology and Experimental Therapeutics 211:502–508 (1979), all of which are herein incorporated by reference.

Briefly, the determination of the $K_i$ or $K_d$ values for use in the $\beta_2/\beta_1$ potency ratio is carried out as described below. Variations of these techniques are possible, and the exact methodology is not critical, so long as $K_i$ or $K_d$ values are derived.

(a) Determination of $K_i$ values for the inhibition of isoproterenol-stimulated adenylate cyclase.

Homogenates or washed particulate preparations (10 mg/ml) in 6 mM Tris-maleate, pH 7.4, are prepared from the various tissues to be studied (e.g., ciliary process, choroid plexus, heart or lung). Adenylate cyclase activity is measured in assay tubes containing (in 0.3 ml) 80 mM Tris-maleate, pH 7.4; 8 mM MgCl$_2$; 10 mM theophylline; 0.03 mM GTP; 2 mM ATP; tissue (1 mg wet weight); 10 μm isoproterenol; and various concentrations of the antagonist to be tested. The enzyme reaction (4 min at 30° C.) is initiated by addition of ATP, stopped by boiling for 2 min, and then centrifuged at 1000×g for 15 min. Cyclic AMP content in the supernatant is determined by binding assay, such as described in Nathanson, Life Sciences 26:1793–1799 (1980). $K_i$ values from these data are calculated by the method of Chen and Prusoff, supra, using the equation described previously (Equation 1).

(b) Determination of $K_d$ values for the inhibition of $^{125}$I-iodohydroxybenzylpindolol (IHYP) binding.

Washed particulate preparations of the above described tissues are suspended in from 200–600 volumes of 0.9% NaCl, containing 20 mM Tris HCl, pH 7.5 (Tris saline). A 0.15 ml aliquot is incubated for 30 min at 37° C. with 40,000–60,000 cpms of IHYP in 0.25 ml of Tris saline. The reaction is stopped by adding 10 ml of Tris saline, and the samples are rapidly filtred through a glass fiber filter. After washing with another 10 ml of Tris saline, radioactivity on the filter is determined via gamma counting. Using Scatchard analysis and appropriate controls for non-specific binding, the $K_d$ value for IHYP binding for various antagonists can be calculated using the method of Chen and Prusoff, supra.

To exemplify the above methods, results for $K_i$ and $K_d$ in ciliary process, heart, and lung, obtained by the present inventor and by Minneman et al, and summarized in Table 1 of the present application, can be used to calculate selective $\beta_2/\beta_1$ potency ratios for drugs shown therein. These ratios are shown in Table 2.

Table III shows the beta$_2$/beta$_1$ potency ratio for beta adrenergic antagonists calculated from $K_i$ heart and $K_i$ ciliary process values obtained by using the above methods.

TABLE III

Calculated beta$_2$/beta$_1$ potency ratios and $K_i$'s of various antagonists for inhibition of rabbit ciliary process and rabbit heart isoproterenol-stimulated adenylate cyclase.

| Drug | Adenylate Cyclase $K_i$ (Micromolar) | | $K_i$ heart |
|---|---|---|---|
| | Ciliary Process beta$_1$ | Heart beta$_2$ | $K_i$ Ciliary Process = beta$_2$/beta$_1$* |
| Practolol | 21.0 | 6.8 | 0.32 |
| Atenolol | 11.0 | 4.1 | 0.37 |
| Butoxamine | 1.40 | 9.5 | 6.8 |
| H35/25 | 0.79 | 7.0 | 8.8 |
| IPS 339 | 0.004 | 0.84 | 210.0 |
| Timolol | 0.0045 | 0.016 | 3.6 |
| Propranolol | 0.0049 | 0.025 | 5.1 |

*±20%.

TABLE II

| | $\beta_2/\beta_1$ potency ratio for $\beta$ adrenergic antagonists | | |
|---|---|---|---|
| Drug | ($K_i$ heart/ $K_i$ ciliary process)(1) | ($K_i$ heart/ $K_i$ lung)(1) | ($K_d$ heart/ $K_d$ lung)(1) |
| Practolol | 0.036 | 0.078 | 0.04 |
| Atenolol | 0.068 | 0.42 | 0.23 |
| Butoxamine | 1.50 | 4.88 | 1.98 |
| H35/25 | 3.1 | 1.58 | 2.3 |
| IPS 339 | 57.0 | — | ≧20 |
| Timolol | N.A. | — | — |
| Propranolol | 3.7 | 4.0 | 2.8 |

(1)See Table I, supra.
(2)The values are accurate to ±20%.

This table demonstrates that there is an approximate correlation between the ratio obtained by the method using $K_i$ values and the method using $K_d$ values. The most relevant ratio for the purposes of the present invention is the $K_i$ heart/$K_i$ ciliary process ratio. However, as stated previously, any method which yields the $\beta_2/\beta_1$ potency ratio can be used.

The drugs useful in the present invention are those which show $\beta_2/\beta_1$ potency ratio greater than 10 in any method. Preferably, the $\beta_2/\beta_1$ potency ratio should be greater than 15, most preferably greater or equal than 20. By independently measuring the $\beta_2/\beta_1$ ratio by the readily accessible methods of the art, it is immediately and routinely possible, without further research or experimentation, to determine whether a beta-adrenergic antagonist falls within the desired class of highly potent and specific drugs used in the present invention.

Table 2 also shows that IPS 339 is the only drug of those listed therein which falls within those of the present invention.

IPS 339 has the following formula:

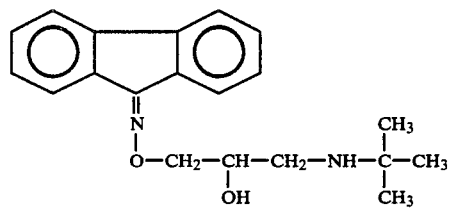

However, other drugs having similar structure to IPS 339 are also useful, particularly those having the formula:

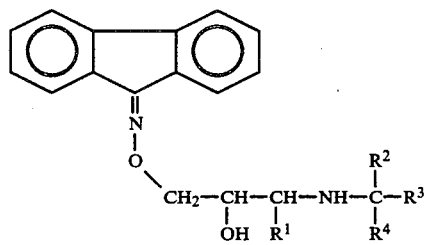

wherein R$_1$–R$_4$ are the same or different lower alkyl groups, preferably C$_1$–C$_4$ alkyl groups; most preferably R$^1$ is hydrogen or methyl.

Any other homologues (lower or higher), analogues (e.g. having other aromatic rings such as naphtyl, and the like) or substituted derivatives (alkyl, halo, nitro, hydroxy, etc.) of the IPS 339 family which are beta$_2$ adrenoceptor antagonists with a $\beta_2/\beta_1$ potency ratio of at least 10, are equivalent for the purposes of this invention. It should be understood, of course, that any beta$_2$ adrenoceptor antagonists having $\beta_2/\beta_1$ potency ratio >10 are included in this invention, including of course any antagonists yet to be discovered.

The determination of whether a drug is a beta antagonist or agonist is also readily carried out, since an agonist (e.g. isoproterenol) stimulates adenylate cyclase activity, whereas an antagonist inhibits agonist stimulation of adenylate cyclase activity.

The $\beta_2$ adrenoceptor antagonists of the present invention are used topically in treating increases in intraocular pressure in mammalian eyes, as for example, by using drops. Other methods of administration can be intravenous administration, oral administration, intraperitoneal administration, intramuscular administration and the like. Topical administration is preferred, as it minimizes systemic side effects. Administration dosage and frequency will depend on the age and general health condition of the patient, taking into consideration the possibility of side effects. Administration will also be dependent on concurrent treatment with other drugs and patient's tolerance of the administered drug. Normally, topical application in amounts of 0.01–10 mg per application of a solution of the antagonist, in one or several daily applications, would be sufficient to decrease intraocular pressure. Treatment can be carried out for any period of time, depending on the severity of the disease. It could range from a single application to extended treatments of up to several years. The antagonists can be administered in their pharmacologically active form, or water or alcohol soluble salts thereof if necessary, such as hydrochlorides, sulfates and the like. The drugs can be administered by themselves if liquid, or in an aqueous solution such as a buffered or saline solution. Other pharmacologically acceptable vehicles for topical application include:

cetyl alcohol, EDTA, glycerin, glyceryl monostearate, isopropyl myristate, mineral oil, petrolatum (white and/or liquid), polyethylene, polyethylene glycol, polyoxyalkylene diol, polyoxyethylene polyoxypropylene, polyoxyl 40 sterate, polysorbate 40 or 80, propylene glycol, sorbitol, stearic acid, and tyloxapol, alone or in combination; plus or minus various preservatives, such as benzyalkonium chloride, butylparaben, chlorobutonol, methylparaben, phenylethyl alcohol, sodium bisulfite, and tyloxapol. The concentration of the active agent will usually range from 0.01% to 99.9% by weight of the composition.

Any type of condition which results from an increase in intraocular pressure in any kind of mammal can be treated according to the methods of the present invention. Various types of glaucoma are included therein, for example, glaucoma absolutum, apoplectic glaucoma, auricular glaucoma, fulminant glaucoma, hemorrhagic glaucoma, glaucoma imminens, infantile glaucoma, inflammatory glaucoma, malignant glaucoma, narrow angle glaucoma, open angle glaucoma, primary glaucoma, secondary glaucoma, and glaucoma simplex.

Having now generally described this invention, the same will be better understood by reference to a specific example which is included herewith for purposes of illustration only and is not intended to be limiting of the invention or any embodiments thereof.

Male, 2-4 kg, New Zealand white rabbits were housed under standard conditions and exposed to a 12 hour light-dark cycle. Intraocular pressure was measured with a Perkins applanation tonometer after topical anesthesia with 0.4% benoxinate (and 0.25% sodium fluorescein). The tonometer had been calibrated previously by connecting the anterior chamber of ennucleated rabbit eyes to a manometer (and reservoir), and taking tonometer readings at different pressures. A large number of preliminary IOP readings were made in order to accommodate the animals to the measurement procedure. These readings indicated reproducible control pressures of 14.02±0.06 mmHg (mean +SEM for 120 measurements). To minimize possible diurnal pressure variations, measurements were made at the same time of day for both drug and control eyes. All drug studies were carried out in a blind fashion with two experimenters, one applying the drug, (or placebo) and the second measuring IOP. The second experimenter had no knowledge as to what drug (or placebos) were applied until the end of the entire study.

Four rabbits received (in two, 50 microliter doses) either 0.5% timolol or 0.5% IPS 339 (mixed in phosphate buffered saline, pH 7.4) in the inferior conjunctival sack of the left or right eye. The contralateral eye received phosphate buffered saline alone. IOP measurements were made on both ipsilateral and contralateral eyes 0, 1, 2, 3, 4 and 6 hours after application, by which time pressure in most drug-treated eyes had returned to normal. Two days later the same four rabbits again received IPS 339 or timolol but to the eyes previously treated with phosphate buffered saline, and IOP was measured as above. This procedure was repeated again at 4 and at 6 days, such that by the end of the experiment each eye had received each drug once but no eye had received more than one drug. All eight eyes, except one, showed consistent responses to drug application. The single eye which did not, failed to respond to either IPS 339 or to timolol. Comparisons between groups and comparisons pre- and post application were calculated both on the basis of including this eye (N=8) or excluding it (N=7). The statistical results were significant using either group size.

In addition to those rabbits above, four others received no drugs but only phosphate buffered saline for the duration of the experiment. IOP measurements for these rabbits, recorded on the same schedule as those described above, revealed no significant change in base line IOP during the course of the study.

Figure 2:
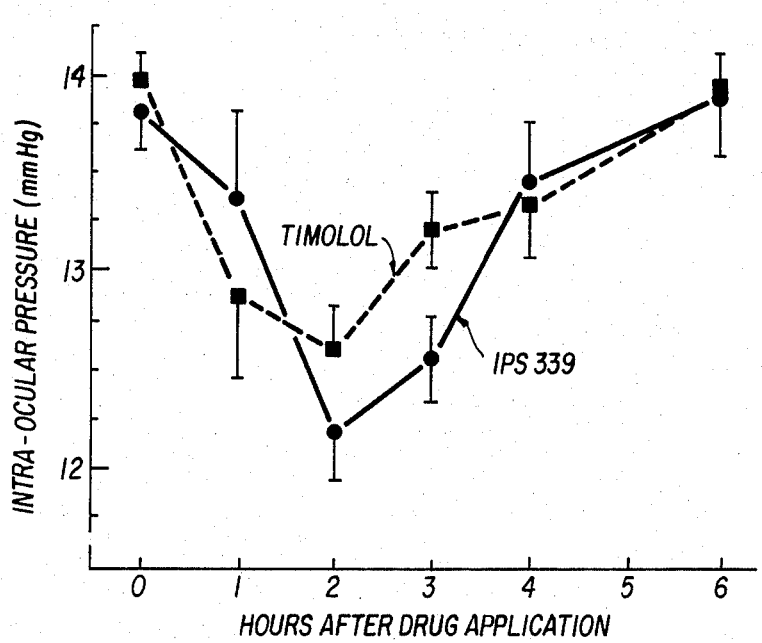
FIG. 2 shows the effects of topically applied 0.5% IPS 339 (●) or 0.5% timolol (■) on intraocular pressure in rabbit eyes. Shown is the mean pressure (±SEM) in mmHg prior to treatment (0 hour) and for 6 hours following drug application.

FIG. 2 shows the mean IOP readings for the 6 hours following the application of either timolol or IPS 339. Compared to predrug readings, both agents caused a significant decrease in IOP in ipsilateral eyes at 2 and 3 hours after application; timolol also caused a significant decrease at 1 hour compared to pre-drug readings. The extent of the decrease caused by the two drugs did not differ significantly except at 3 hours, at which time the decrease caused by IPS 339 was significantly more than that caused by timolol. During the course of the experiment, no significant changes in pupillary diameter nor overt ocular toxicity were noted for either drug. In addition to decreasing pressure in the ipsilateral eye, both drugs also caused a significant decrease in IOP in the contralateral eye. The magnitude of this effect, which has been reported previously for timolol, and is presumably due to a systemic absorption of the drug, was somewhat less for IPS 339 than for timolol.

This data indicates that the specific beta$_2$ antagonist IPS 339 is very effective in decreasing IOP in the normal rabbit eye. This effect is also observed under conditions of elevated pressure. Specifically, intraocular pressure above normal produced by alpha chymotrypsin-induced glaucoma in rabbits is also decreased significantly by the $\beta_2$ antagonist IPS 339, compared with the non-specific $\beta_1$-$\beta_2$ antagonist, timolol.

The present results, in view of the inventor's discovery of the presence of specific beta$_2$ adrenoceptors in the ciliary process of mammalian eyes, indicate that potent and highly specific beta$_2$ adrenergic antagonists as a group are effective in reducing elevated IOP.

Having now fully described this invention it will be understood by those skilled in the art that many modifications and variations can be carried out without affecting the spirit or scope of the invention or any embodiments therof.

What is claimed as new and intended to be covered by Letters Patent is:

1. A method of decreasing the intraocular pressure in the eye of an animal which comprises topically administering to said animal an intraocular pressure-decreasing amount of a $\beta_2$ adrenergic receptor antagonist which has the formula:

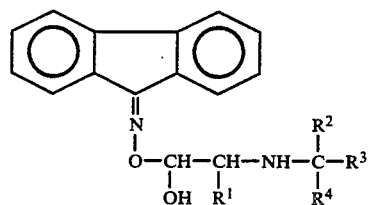
wherein $R^1$, $R^2$, $R^3$ and $R^4$ are the same or different selected from the group consisting of hydrogen and lower alkyl radicals.
2. The method of claim 1, wherein $R^1$ is hydrogen and $R^2 = R^3 = R^4 =$ methyl.
3. The method of claim 1, wherein $R^1$ is methyl.
* * * * *